United States Patent
Schloemer et al.

(10) Patent No.: US 6,372,946 B1
(45) Date of Patent: Apr. 16, 2002

(54) PREPARATION OF 4,4'-DIKETO-β-CAROTENE DERIVATIVES

(75) Inventors: George C. Schloemer; Danuta A. Schloemer, both of Longmont; Jeffery L. Davis, Berthoud, all of CO (US)

(73) Assignee: Prodemex, S.A. DE C.V., Los Mochis (MX)

( * ) Notice: Subject to any disclaimer, the term of this patent is extended or adjusted under 35 U.S.C. 154(b) by 0 days.

(21) Appl. No.: 09/953,007

(22) Filed: Sep. 13, 2001

(51) Int. Cl.[7] .............................................. C07C 45/00
(52) U.S. Cl. ........................ 568/347; 568/348; 568/362; 568/374
(58) Field of Search ................................ 568/347, 348, 568/362, 374

(56) References Cited

U.S. PATENT DOCUMENTS

| | | | |
|---|---|---|---|
| 4,212,827 A | * | 7/1980 | Paust et al. |
| 5,565,357 A | * | 10/1996 | Tsubokura et al. |
| 5,625,099 A | * | 4/1997 | Ernst et al. |
| 6,313,352 B1 | * | 11/2001 | Mori et al. |

OTHER PUBLICATIONS

Sakaguchi, S., et al. "Oxidation of Diols and Ethers by $NaBrO_3/NaHSO_3$ Reagent," (1997) Bull. Chem. Soc. Jpn. 70:2561–2566.

Masuda, H., et al. "A New Synthetic Method of Preparing Iodohydrin and Bromohydrin Derivatives through in Situ Generation of Hypohalous Acids from $H_5IO_6$ and $NaBrO_3$ in the Presence of $NaHSO_3$," (1994) J. Org. Chem. 59:5550–5555.

Ohta, H., et al., "Iodohydrin Synthesis from Simple and Functionalised Olefins on Treatment with Periodic Acid and Sodium Bisulfite," (1990) Chemistry Letters, pp. 733–736.

* cited by examiner

Primary Examiner—Johann Richter
Assistant Examiner—Sikarl A. Witherspoon
(74) Attorney, Agent, or Firm—Knobbe, Martens, Olson & Bear, LLP

(57) ABSTRACT

A method of preparing β-carotene derivatives such as canthaxanthin and astaxanthin is described. The method employs an in situ system to generate hypobromous acid as the oxidizing agent using a salt of sulfite, hydrogen sulfite or bisulfite in combination with a bromate salt. Astaxanthin and canthaxanthin are obtained in good yield with a significantly reduced reaction time.

8 Claims, No Drawings

PREPARATION OF 4,4'-DIKETO-β-CAROTENE DERIVATIVES

BACKGROUND OF THE INVENTION

1. Field of the Invention

The present invention relates to a method of direct oxidative conversion of β-carotene and β-carotene derivatives such as 3,3'-dihydroxy-β-carotene (zeaxanthin) to 4,4'diketo-β-carotene and 3,3'-dihydroxy-4,4'-diketo-β-carotene (astaxanthin), respectively. In this manner, canthaxanthin, which is a commercial poultry food additive, and astaxanthin, which is a commercial fish food additive, can be prepared from inexpensive naturally derived starting materials.

2. Description of the Related Art

Commercially, astaxanthin is an economically important natural carotenoid which is extensively used in aquaculture to impart natural color in certain species of fish, specifically salmon and trout, as these fish do not have access to these natural pigmentation sources. Likewise, canthaxanthin is a reddish natural pigment which is used in the poultry industry to impart color to the egg yolk and skin. Both compounds are prepared synthetically.

Astaxanthin can be prepared by total synthesis or by algae culture and bacterial fermentation (See, for example, U.S. Pat. Nos. 6,022,701, 6,015,684, 5,972,642 and 5,935,808). The manufacture by total synthesis is costly, requiring expensive raw materials and reagents and is very laborious. The synthesis produces a complete mixture of isomers that are normally not found in nature. The culturing of algae and the fermentation of bacteria produce only low yields of product and mixtures including other carotenoids which make them not suitable for food additives. Likewise, these methods are very costly.

We (patent application No. 09/813,685) have previously described the conversion of zeaxanthin to astaxanthin but the present method provides a cleaner reaction and higher yields. The synthetic conversion of β-carotene to canthaxanthin has been previously described (U.S. Pat. No. 4,212,827). However, this procedure employs expensive iodide reagents or molecular bromine in order to carry out the oxidation. The present procedure employs hypobromide instead of molecular bromine and does not need the 5 day reaction indicated in the above-cited patent. Masuda et al. (Masuda et al. J. (1994) Org. Chem. 59: 5550–5555) reported that hypobromous acid (BrOH) can be generated from $NaBrO_3$ and $NaHSO_3$. Sakaguchi et al. (Sakaguchi et al. (1997) Bull. Chem. Soc. Jpn. 70: 2561–2566) reported that the above reagent can be used in oxidation of various diols to form ketones. However, the use of hypobromide in the oxidation of complex biomolecules such as β-carotene and zeaxanthin to form commercially important pigments has not been reported. The presently disclosed method provides a distinct advantage over previously described methods in that the reaction time is significantly reduced.

SUMMARY OF THE INVENTION

In one embodiment of the invention a method of preparing 4,4'-diketo derivatives from β-carotene or β-carotene derivatives is described which includes contacting the β-carotene or β-carotene derivatives in an organic solvent with a solution of an oxidizing agent, wherein the oxidizing agent is formed by mixing acidified aqueous solutions of the sodium or potassium salts of sulfite, hydrogen sulfite, or bisulfite solutions and sodium or potassium bromate solutions in water to produce 4,4'-diketo derivative products. In one embodiment, the β-carotene derivative is zeaxanthin and the product is astaxanthin. In an alternate embodiment, β-carotene is employed and the product is canthaxanthin.

In one embodiment of the described method, the oxidizing agent is formed by addition of an acidified solution selected from the group including sodium or potassium sulfite, sodium or potassium hydrogen sulfite, and sodium or potassium bisulfite to a biphasic media consisting of β-carotene or β-carotene derivatives in an organic solvent and either sodium bromate or potassium bromate in an aqueous solvent. In a preferred embodiment, the oxidizing agent is formed by mixing aqueous solutions selected from the group including acidified sodium or potassium sulfite, acidified sodium or potassium hydrogen sulfite, and acidified sodium or potassium bisulfite with aqueous solutions of either sodium bromate or potassium bromate and adding the resulting solution to an organic solvent solution of β-carotene or β-carotene derivatives. In a most preferred embodiment, the aqueous solution is acidic. In a preferred embodiment, the β-carotene derivative is zeaxanthin and the product is astaxanthin. In an alternate preferred embodiment, β-carotene is employed and the product is canthaxanthin.

In a preferred embodiment of the described method, the organic solvent is chloroform or methylene chloride.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

The present invention relates to a method for the oxidative conversion of β-carotene and β-carotene derivatives to the corresponding 4,4'-diketo-β-carotene derivatives. Compounds of economic importance such as canthaxanthin and astaxanthin can be formed readily from β-carotene and zeaxanthin by the disclosed method. The method includes contacting zeaxanthin or β-carotene in an organic solvent with an oxidizing agent formed by the addition of salts of sulfite, hydrogen sulfite or bisulfite to an aqueous solution of a bromate salt. In a preferred embodiment, the salt is a sodium or potassium salt.

In one embodiment, the reaction solvent is a halogen containing solvent and the pH of the solution is acidic. The bromate and sulfite can be mixed either prior to the reaction or added later during the reaction itself. In a preferred embodiment, zeaxanthin or β-carotene is slurried or dissolved in chloroform and an aqueous solution containing sodium or potassium bromate. An aqueous solution of sodium hydrogen sulfite is added slowly to effect the reaction. In another preferred embodiment, an aqueous solution of the oxidant is prepared by mixing sodium bromate and sodium hydrogen sulfite and this solution is added to the chloroform solution or slurry of zeaxanthin or β-carotene to effect reaction.

The present invention also may have some utility in the formation of 4,4'-keto groups of other carotenoid compounds. Such compounds include but are not limited to echinenone, astacene, phoenicopterone, 3-hydroxycanthaxanthin, and 3,3'-dihydroxyechinenone.

The present invention is directed toward a method of treating β-carotene and β-carotene derivatives with an oxidizing agent. Non-limiting examples of performing allylic oxidations or agents that may be employed in oxidation reactions have been reviewed in Barry Trost and Ian Fleming, eds. "Comprehensive Organic Synthesis", Volume 7, Pergamon Press, New York, 1991, Pages 83–117, and Richard C. Larock "Comprehensive Organic Transformations", Wiley-VCH, New York, 1999, pages 1207–1209, which are incorporated herein in their entirety by reference. However, most of these conditions produce substantial or complete decomposition of the sensitive β-carotene structure. In contrast, in the preferred embodiment of this invention the double allylic oxidation of this sensitive structure can be carried out in good yield. Preferably, zeaxanthin with or without a blocking group on the alcohol moiety can be oxidized directly to astaxanthin or astaxanthin derivatives by the activity of an oxidant derived from sodium or potassium bromate and sodium hydrogen sulfite or sodium metabisulfite under acidic conditions.

In one embodiment of the invention, the reaction is carried out in a two-phase system utilizing a chlorinated solvent in the second phase along with the aqueous phase of sodium or potassium bromate to which is added a solution of sodium hydrogen sulfite. In a preferred embodiment, the organic solvent is chloroform and the aqueous solution is pH=1–3. Also, preferably, an oxidizing solution can be prepared and stored by mixing together sodium or potassium bromate and either an acidified solution of sodium sulfite or solutions of sodium hydrogen sulfite or sodium metabisulfite. Preferably the pH of the resulting media is between pH=1–3.

In an alternative embodiment, β-carotene instead of zeaxanthin can be employed as the starting material and the reaction will produce canthaxanthin.

In one embodiment of the invention, the ratio of oxidizing agent relative to zeaxanthin or β-carotene can vary between a catalytic amount to 2 molar equivalents. The term "catalytic amount" refers to an amount of the oxidizing agent that is less than the stoichiometric quantity of the zeaxanthin or β-carotene used in the reaction. The term "stoichiometric" refers to the use of an equivalent mole ratio or amount of a reagent relative to a selected substrate, molecule or compound in the reaction.

In one embodiment of the invention, the reaction is carried out in a two phase system with an inert organic solvent layer and an aqueous layer. The organic layer can be any inert solvent, but preferably, chloroform or methylene chloride are used.

In one embodiment of the invention, the ratio of zeaxanthin or β-carotene to organic solvent varies from 1:10 to 1:500 depending upon the reaction conditions. Preferably, the ratio of zeaxanthin or β-carotene to the organic solvent is from about 1:10 to about 1:200.

In one embodiment, the reaction is conducted under acidic conditions. In a preferred embodiment, the pH of the reaction media can be from pH=0 to pH=6. In a most preferred embodiment, the pH is between 1–3. Any non-reactive acid may be employed to adjust acidity. In a preferred embodiment, the acidity is increased by the addition of sulfuric acid.

In one embodiment of the invention, the temperature of the reaction may vary from 0° C. to 50° C. In a preferred embodiment, the reaction is carried out between 10° C. and 40° C.

It will be understood by those of skill in the art that numerous and various modifications can be made without departing from the spirit of the present invention. Therefore, it should be clearly understood that the forms of the present invention are illustrative only and are not intended to limit the scope of the present invention.

EXAMPLE 1

Oxidant Reagent Preparation

Sodium bromate (3.2 grams) were dissolved in 24 ml of water with stirring. In a separate flask, 1.6 grams of sodium hydrogen sulfite were dissolved in 24 ml of water. The solutions were mixed together. Any bromine that formed was allowed to evaporate. The clear, colorless solution was used in the following reaction.

Zeaxanthin to Astaxanthin

Zeaxanthin (0.275 gm, 0.48 mole) obtained from natural sources in 55% purity was slurried in 10 ml of chloroform. At room temperature, 1.6 ml of the oxidant reagent of Example 1 was added. The mixture was stirred rapidly for 30 minutes. The layers were separated and the organic layer was washed with 5 ml of water. The organic layer was concentrated to 5 ml and 20 ml of hexane was added. A precipitate formed and was filtered off. The filtrate was concentrated to dryness and the residue was dissolved in 5 ml of absolute ethanol. The dissolved residue was then washed with 4 ml of water. The mixture was cooled to 5° C. and filtered. The solid was washed with 20% ethanol in water. The solid was dried to produce 0.14 gms (51%) of astaxanthin product containing greater than 30% astaxanthin by weight.

EXAMPLE 2

Zeaxanthin to Astaxanthin

To a suitable flask was added 20 grams of a natural product mixture containing 12.2 grams zeaxanthin (21.4 mmoles) slurried in 200 ml of chloroform. To this mixture was added a solution of 8.05 gms (53.3 mmoles) of sodium bromate. To this mixture was added dropwise over three hours at temperatures between 20 to 30° C., 8 ml of a solution prepared by dissolving 6.66 gms of sodium metabisulfite in 24 ml of water. After addition, the reaction mixture was filtered through Celite and the aqueous phase was separated. The chloroform was removed by vacuum evaporation at 40–42° C. The resulting slightly wet solid was added to 190 ml of warm (50° C.) 95% ethanol. The mixture was stirred and cooled slowly to −10° C. The resulting solid was filtered off and dried under vacuum to produce 8.8 grams (72.14%) yield of astaxanthin product containing greater than 25% astaxanthin.

EXAMPLE 3

β-Carotene to Canthaxanthin

Into a flask was charged 0.5 gm of β-carotene and 10 ml of chloroform. The mixture is stirred to form a solution. Into this solution was charged 1.6 ml of the oxidant solution described in example 1. The mixture was stirred for 1.5 hours to complete the reaction. The phases were separated and the organic phase was washed with water once and evaporated to yield a residue that was dissolved in 10 ml of warm ethanol. This ethanol solution was added slowly to 50 ml of water to form a precipitate which was filtered and dried to yield 85% yield of canthaxanthin of approximately 80% purity.

What is claimed is:

1. A method of preparing 4,4'-diketo derivatives from β-carotene or β-carotene derivatives comprising contacting the β-carotene or β-carotene derivatives in an organic solvent with a solution of an oxidizing agent, wherein said oxidizing agent is formed by mixing acidified aqueous solutions of the sodium or potassium salts of sulfite, hydrogen sulfite, or bisulfite solutions and sodium or potassium bromate solutions in water to produce 4,4'-diketo derivative products.

2. The method of claim 1, wherein said β-carotene derivative is zeaxanthin and the product is astaxanthin.

3. The method of claim 1, wherein said oxidizing agent is formed by addition of an acidified solution selected from the group consisting of sodium or potassium sulfite, sodium or potassium hydrogen sulfite, and sodium or potassium bisulfite to a biphasic media comprising β-carotene or β-carotene derivatives in an organic solvent and either sodium bromate or potassium bromate in an aqueous solvent.

4. The method of claim 1, wherein said oxidizing agent is formed by mixing aqueous solutions selected from the group consisting of acidified sodium or potassium sulfite, acidified sodium or potassium hydrogen sulfite, and acidified sodium or potassium bisulfite with aqueous solutions of either sodium bromate or potassium bromate and adding the resulting solution to an organic solvent solution of β-carotene or β-carotene derivatives.

5. The method of either of claim 3 or claim 4, wherein the organic solvent is chloroform or methylene chloride.

6. The method of either of claim 3 or claim 4, wherein said β-carotene derivative is zeaxanthin and the product is astaxanthin.

7. The method of claim 1, wherein β-carotene is employed and the product is canthaxanthin.

8. The method of either of claim 3 or claim 4, wherein β-carotene is employed and the product is canthaxanthin.

* * * * *